United States Patent
Matson et al.

(10) Patent No.: US 11,319,499 B1
(45) Date of Patent: May 3, 2022

(54) BIOMASS PRETREATMENT WITH INTEGRAL FOSSIL FUEL BLENDING

(71) Applicants: Theodore Matson, Charlottesville, VA (US); Michael Gurin, Glenview, IL (US)

(72) Inventors: Theodore Matson, Charlottesville, VA (US); Michael Gurin, Glenview, IL (US)

(73) Assignee: Michael Gurin, Glenview, IL (US)

( * ) Notice: Subject to any disclaimer, the term of this patent is extended or adjusted under 35 U.S.C. 154(b) by 0 days.

(21) Appl. No.: 16/990,029

(22) Filed: Aug. 11, 2020

Related U.S. Application Data

(60) Provisional application No. 62/886,214, filed on Aug. 13, 2019.

(51) Int. Cl.
*C10L 1/02* (2006.01)
*C07C 51/00* (2006.01)
*C07D 307/50* (2006.01)

(52) U.S. Cl.
CPC ............ *C10L 1/02* (2013.01); *C07C 51/00* (2013.01); *C07D 307/50* (2013.01); *C10L 2200/0438* (2013.01); *C10L 2200/0469* (2013.01); *C10L 2290/08* (2013.01); *C10L 2290/24* (2013.01); *C10L 2290/543* (2013.01); *C10L 2290/547* (2013.01)

(58) Field of Classification Search
CPC ............ C10L 1/02; C10L 2290/547; C10L 2290/543; C10L 2200/0469; C10L 2290/24; C10L 2290/08; C10L 2200/0438; C07C 51/00; C07D 307/50
See application file for complete search history.

(56) References Cited

U.S. PATENT DOCUMENTS

2021/0214617 A1* 7/2021 Seidner ............... C10G 1/045

OTHER PUBLICATIONS

Meng et al.; "Chemical Transformations of Poplar Lignin during Cosolvent Enhanced Lignocellulosic Fractionation Process", ACS Sustainable Chem. Eng. 2018, 6, 8711-8718; (Year: 2018).*
Wyman et al.; "Co-Solvent Enhanced Lignocellulosic Fractionation (CELF) to Produce Precursors for Biological and Catalytic Conversion to Fuels and Chemicals", Dec. 8, 2014 (Year: 2014).*
Oiltanking; "Heavy Fuel Oil (HFO) Glossary", Aug. 16, 2019 (Year: 2019).*

* cited by examiner

*Primary Examiner* — Ellen M McAvoy
*Assistant Examiner* — Chantel L Graham

(57) ABSTRACT

A blended homogeneous oil composition and blending method with reduced environmental footprint using a blend of a biomass liquefaction oil derived from solvolysis with an integral fossil-based oil component. The resulting blended product has a reduced capital cost for the blending system and a reduced per barrel costs as compared to a non-blended biomass derived oil composition.

20 Claims, 5 Drawing Sheets

Two types of methoxyl group C1 and C2 in lignin Non-Solvolysis Oil pyrolysis oil Methoxyl groups in the HSQC–NMR spectra of Non-Solvolysis Oil pyrolysis oils Special aliphatic carbons in Non-Solvolysis Oil pyrolysis oil $^1$H and $^{13}$C NMR chemical-shift distributions of various functional groups for compounds reported present in Non-Solvolysis Oil pyrolysis oils (horizontal axis in ppm)

Detailed Structures of Assignments for HSQC–NMR Analysis of Non-Solvolysis Oil

BIOMASS PRETREATMENT WITH INTEGRAL FOSSIL FUEL BLENDING

CROSS-REFERENCE TO RELATED APPLICATIONS

This application claims the benefit of provisional patent application U.S. No. 62/886,214 filed on Aug. 13, 2019 titled "Biomass pretreatment with integral fossil fuel blending", and hereby incorporated by reference in their entirety.

FIELD OF INVENTION

The present invention relates to the strategic use of fossil fuel blending to both decrease the production and capital costs of biomass pretreated bio derived liquids and to lower the environmental footprint of the resulting product.

BACKGROUND OF INVENTION

Prior art focuses on a wide range of pretreatment or liquefaction processes including the thermochemical conversion of biomass involving high temperature reactions (>300 C) that simultaneously promote the deconstruction of the carbohydrates and lignin components, but also result in unwanted degradation products due to the severe reaction conditions. First generation thermochemical conversion methods include gasification, pyrolysis, and hydrothermal liquefaction. In all these reactions, byproducts such as CO2 gas, carbon-rich black chars, and insoluble highly condensed tars or resins would form alongside desired intermediates such as syngas, pyrolysis/bio-oil, or biocrude.

In the latest advancement in thermochemical conversion techniques, a new generation of technologies called acid "solvolysis" methods that use co-solvents have been able to achieve liquefaction and fractionation of solid lignocellulosic biomass feedstocks without significant formation of unwanted byproducts. As a result, at much lower temperatures of less than 250 C, solvolysis methods could liquefy and fractionate lignin, cellulose, and hemicellulose fractions from biomass into a homogenous liquid product without causing significant degradation to carbon dioxide, chars, and tars. One of the most notable solvolysis methods of late is known as the Co-solvent Enhanced Lignocellulosic Fractionation (CELF) method (DOI: 10.1039/C3GC41214H and DOI: 10.1002/CSSC.201403045). This method involves the use of polar aprotic tetrahydrofuran (THF) as a miscible co-solvent with water during dilute acid-catalyzed treatment of biomass to further enhance the solubilization of lignin and hydrolysis of cellulose. The liquor or liquids produced by CELF treatment of biomass is notable for its high concentration of dissolved depolymerized lignin and monomeric furfurals that are suitable as blending components to heavy residual oils from petroleum, enabling the creation of stable blended heavy fuel oils containing up to 70% biomass-derived materials that can be used as a fuel serving marine transportation and stationary power generation, or used as a feed for coking operations.

Conventionally, treatment or pretreatment of biomass at milder temperatures (<250 C) with dilute acids (<5% acid by weight) in water-only reactions resulted in only the significant hydrolysis and solubilization of the hemicellulose fraction of biomass and the cross-condensation of sugars with themselves and with lignin, leading to a resinous product that cannot be blended with petroleum fractions to produce a stable product. These pretreatment techniques were largely applied to produce a pretreated solid biomass material that was more amenable to enzymatic hydrolysis or microbial conversion, different than the purpose described in this invention.

Wood oils or biomass oils produced by solvolysis are not exclusive to CELF, as other solvolysis methods employing co-solvents such as gamma-valerolactone (GVL) have demonstrated similar results. For simplicity, the solvolysis product from the CELF reaction is hereinafter referred to as "CELF wood oil" (irrespective of whether the biomass is wood or other lignocellulosic feedstocks), and pre-treatment as such not by CELF is hereinafter referred to as "solvolysis oil".

SUMMARY OF INVENTION

The present invention is the simultaneous process of distillation of a CELF liquor continuously mixed with a Fossil-based Blend Recipient to produce a Blended Product.

A further object of the present invention is the simultaneous process of distillation of an additional solvolysis liquor continuously mixed with a Fossil-based Blend Recipient to produce a Blended Product.

Yet another object of the invention is a distillative blending method for simultaneous distillation and blending of a CELF liquor with HSRFO to create a stable blended oil containing up to 70 wt % (and at least 10 wt %) biogenic or biomass-derived carbon.

Another object of the invention is distillative blending method for simultaneous distillation and blending of a Blendable Oil liquor with a Fossil-based Blend Recipient to create a stable Blended Product containing up to 70 wt % biogenic or biomass-derived carbon.

Another objective of the invention is to create a Blended Product that is defined as a stable emulsion that does not rapidly settle into two distinct phases if it is maintained at 100 C or greater.

DEFINITIONS

Figure 1:
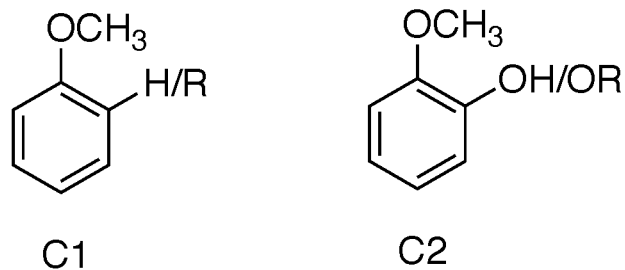
FIG. 1 is a chemical structure of two types of methoxyl group C1 and C2 in lignin Non-Solvolysis Oil pyrolysis oil.

The term "CELF Oil" refers to the particularly preferred water-insoluble and THF-soluble fraction resulting from the CELF solvolysis of lignocellulosic biomass.

The term "Solvolysis Oil" refers to the particularly preferred water-insoluble and co-solvent-soluble fraction resulting from the solvolysis of lignocellulosic biomass.

The term "Blendable Oil" refers to either the preferred CELF Oil (when co-solvent is THF) or Solvolysis Oil, defined as the water-insoluble and co-solvent-soluble fraction resulting from solvolysis of lignocellulosic biomass at solvolysis temperatures greater than 170 C It is understood that each exemplary reference to THF is in relationship to the preferred CELF process and is interchangeable in terms of the relationship to other co-solvents with relationship to non-THF solvolysis processes.

Blendable Oil is the resulting co-solvent-soluble portion of the resulting CELF wood oil after removal of the co-solvent THF from the CELF liquor (CELF liquefaction product still having the THF (i.e., co-solvent) from the post-CELF liquor. The post-CELF liquor is comprised of two distinct phases: a water-soluble distillate phase, and the Blendable Oil (i.e., CELF wood oil residual phase). The Blendable Oil is isolated by simply distilling the CELF liquor and boiling-out the co-solvent THF from the CELF liquor. Upon removal of THF from the CELF liquor, CELF oil components that were once fully soluble in the THF-water co-solvent mixture will separate into two distinct phases. It is important to note that CELF oil can be functionally defined as the high-boiling (greater than 250 C) or non-boiling residual fraction of CELF liquor once the distillates are removed.

The term "Blended Product" refers to the finished product that is a stable emulsion between biogenic and fossil-derived components that does not rapidly settle into two distinct phases if it is maintained at 100 C or greater and can be re-emulsified if stored at a temperature below 100 C. A preferred Blended Product does not phase separate within 2 hours of blending, specifically preferred does not phase separate within 1 day of blending, and particularly preferred does not phase separate within 1 week of blending. Maintaining a stable emulsion of greater than 30 days is achieved as a result of the inventive blending process.

DETAILED DESCRIPTION OF INVENTION

Here, as well as elsewhere in the specification and claims, individual numerical values and/or individual range limits can be combined to form non-disclosed ranges.

Exemplary embodiments of the present invention are provided, which reference the contained figures. Such embodiments are merely exemplary in nature. Regarding the figures, like reference numerals refer to like parts.

Although it has been shown that the CELF method can be applied at lower temperatures (<170 C) as a biomass pretreatment to partially liquefy biomass and produce a glucan-rich solid suitable for enzymatic hydrolysis or fermentation, the preferred CELF method is shown for complete liquefaction of biomass, or acid solvolysis, occurs at higher temperatures (>170 C) hereinafter referred to as CELF Solvolysis. After CELF Solvolysis of biomass, the addition of THF as a co-solvent to water, between the volume ratios of 2:1 and 5:1 THF:water, with biomass is tuned in dilute acid reactions using sulfuric acid or metal halide acids such as ferric chloride to achieve significant liquefaction of the biomass by rapid solubilization and hydrolysis of the hemicellulose, cellulose, and lignin fractions. It is recognized that CELF has been used as both a pretreatment method as well as a solvolysis method, depending on co-solvent concentrations, reaction temperature, and acid concentration. In certain reactions with CELF at temperatures higher than 170 C, up to 99% of woody biomass is solubilized into a homogeneous "wood oil" without the formation of carbon dioxide, chars, or tars (DOI: 10.1039/C4GC00747F). This "wood oil" produced by CELF is otherwise known as CELF wood oil and is homogeneously contained within the post-CELF liquor (post-process CELF wood oil still including the co-solvent THF and water from the CELF reaction). Because CELF causes selective hydrolysis followed by dehydration, non-oil compounds produced by the CELF reaction remain only in the CELF liquor and can be separated out from the CELF oil by distillation.

The fundamental invention unique to the production of Blendable Oil resulting from the solvolysis process such as wood oils or CELF wood oils (it is understood that wood oil is used interchangeably as lignin containing oil whether the biomass is from wood, agricultural matter, or waste products that contain lignin) is the ability for this oil to be more compatible for blending with fossil-derived products containing residual fuel oils (RFO), bitumen, and even coal tar pitch. Without being bound by theory, the reason that Blendable Oil may be a significantly better blendstock for residual fuel oil and bitumen is due to the lack of highly condensed tars, chars, and water-soluble components that are typically found in bio-oil derived from pyrolysis and/or biocrude from hydrothermal liquefaction. Unique to solvolysis oils, including CELF process wood oil, is the removal of all water from the oil prior to any blending or further use. Typically, with pyrolysis oil and HTL biocrude, removal of water would cause substantial (>5 wt %) sedimentation and precipitation of insoluble products.

From molecular and structural analysis data, Blendable Oil produced from hardwoods can be differentiated from other bio-oils, pyr-oils (i.e., pyrolysis oils), and bio-crudes from hardwoods by using 2D Heteronuclear Single-Quantum Correlation-Nuclear Magnetic Resonance (HSQC NMR). The largest differences between lignin and pyrolysis oils exist in the aliphatic region. Two kinds of methoxy groups (C1 and C2) were typically observed in the pyrolysis oil (FIG. 1). There is no C1 type of methoxyl groups (no hydroxyl or ether bond in the ortho position of the methoxyl group) in Blendable Oil and native biomass lignin, suggesting that this kind of $OCH_3$ is formed during the non-inventive pyrolysis process via a decomposition and rearrangement pathway. The non-inventive resulting oil (i.e, pyrolysis oils or other non-solvolysis resulting oils), hereinafter referred to as "Non-Solvolysis Oil" has virtually all (preferably greater than 50%, and particularly preferred greater than 85%) of the lignin inter-linkages including β-aryl ether, phenylcoumaran, and resinol subunits disappeared in the aliphatic region. Extensive amounts of aliphatic carbons are formed in the non-inventive pyrolysis oil due to the rearrangement of ether bonds and the cleavage of lignin side chains.

HSQC cannot provide quantitative or even semi-quantitative data for Non-Solvolysis Oil, because unlike lignin, there is no good internal standard that exists in Non-Solvolysis Oil. Thus, it is challenging to provide pure quantitative data as any kind of evidence showing whether the unknown sample being analyzed is a CELF oil or pyrolysis oil (though difficult to quantify differential, it is clear that Non-Solvolysis Oil is not a suitable Blendable Oil). However, we can tell which kind of functional group exists in Non-Solvolysis Oil, and at the same time, we know for a fact that native lignin (present in Blendable Oil) does not have these kinds of functional groups.

Figure 2:
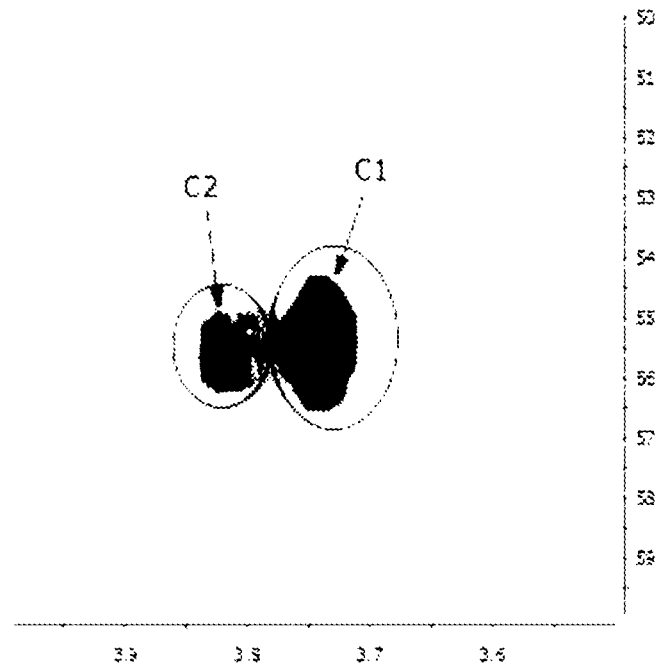
FIG. 2 is a HSQC-NMR spectra of the Non-Solvolysis Oil.

Turning to FIG. 1, FIG. 1 is a perspective highlighting two major differences used to differentiate the inventive Blendable Oil from the non-inventive Non-Solvolysis Oil. First major difference is that two types of methoxy groups C1 (3.9/55.4 ppm) and C2 (3.7/55.7 ppm) were typically observed in the Non-Solvolysis Oil pyrolysis oil (as shown in FIG. 2), while there is no C1 type of methoxyl groups in the inventive Blendable Oil structure that more resembles depolymerized lignin due to the prior removal of carbohydrates.

Figure 3:
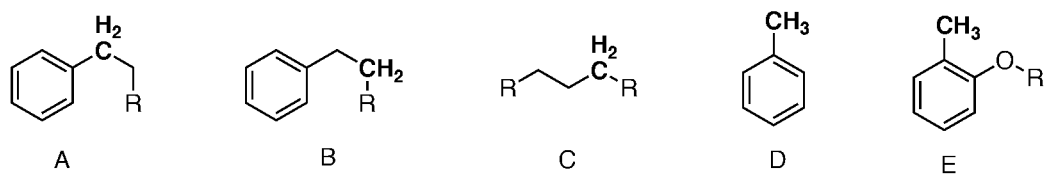
FIG. 3 is chemical structures of special aliphatic carbons of the Non-Solvolysis Oil.

Turning to FIG. 3, FIG. 3 depicts methyl/methylene groups or aliphatic carbons as typically observed in the HSQC NMR of pyrolysis oil in the aliphatic range of $\delta_H$ 1.0-4.0 ppm and $\delta_C$ 10-40 ppm. The formation of these aliphatic carbons is due to the rearrangement of ether bonds or the cleavage of side chains in lignin, and they do not exist in Blendable Oil.

Figure 4:
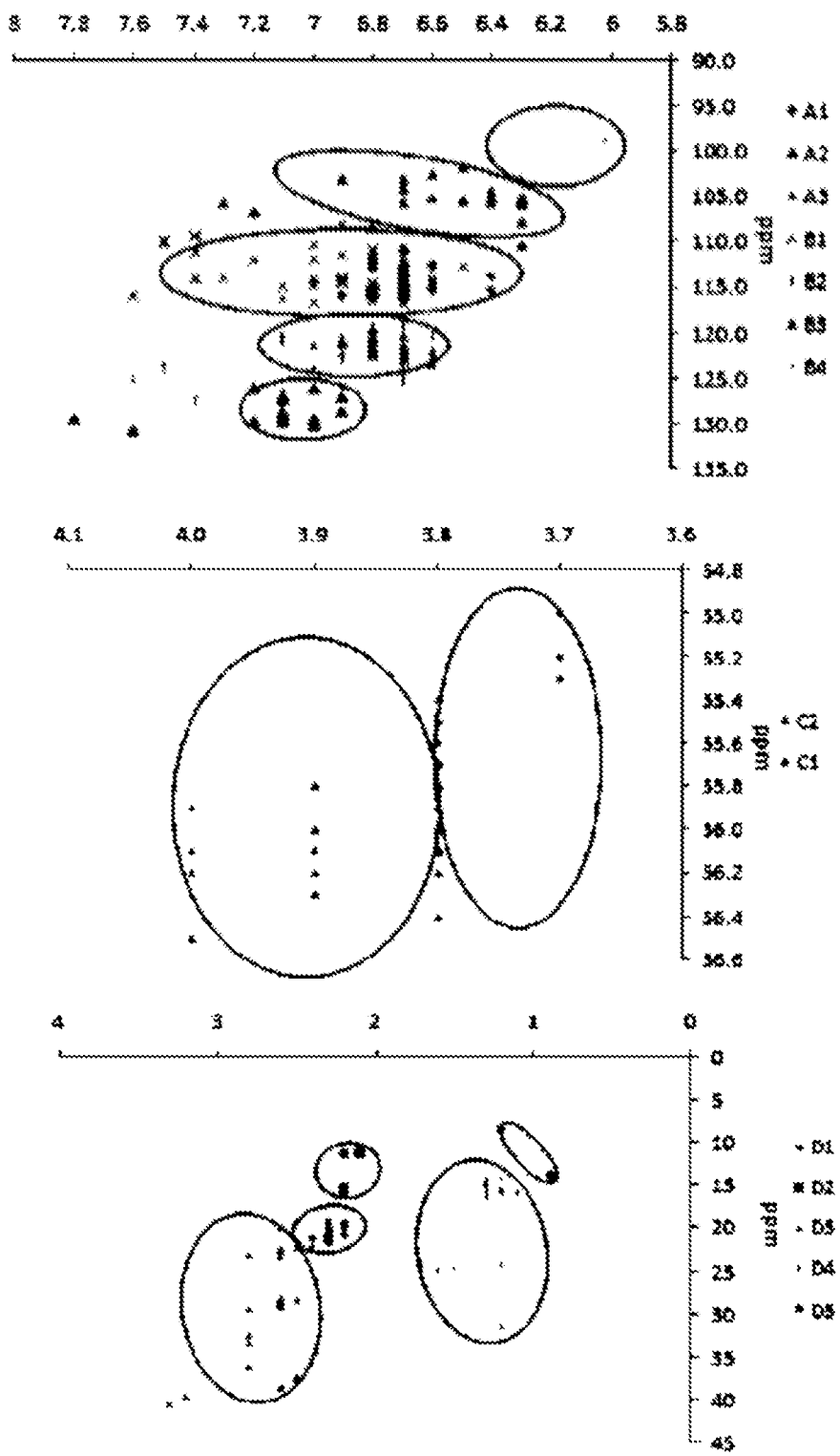
FIG. 4 is a $^1$H and $^{13}$C NMR chemical-shift distributions of various functional groups for compounds reported present in the Non-Solvolysis Oil.

Turning to FIG. 4, FIG. 4 depicts the $^1H$ and $^{13}C$ NMR chemical-shift distributions of various functional groups for compounds reported present in Non-Solvolysis Oil pyrolysis oils.

Figure 5:
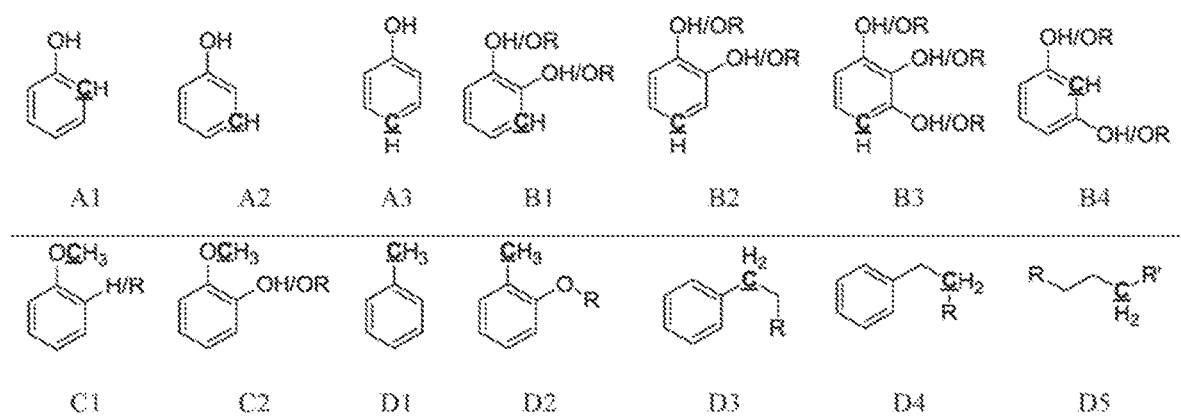
FIG. 5 is chemical structures of assignments for HSQC-NMR Analysis of Non-Solvolysis Oil.

Turning to FIG. 5, FIG. 5 depicts the functional groups of FIG. 4. C1, D1, D2, D3, D4, and D5 are Non-Solvolysis Oil pyrolysis oil structures that are not present in native lignin. Levoglucosan is one of the major products in Non-Solvolysis Oil pyrolysis oil derived from the cellulose of biomass. Furans are also present representing the major aromatic products primarily derived from the hemicellulose of biomass.

Figure 6:
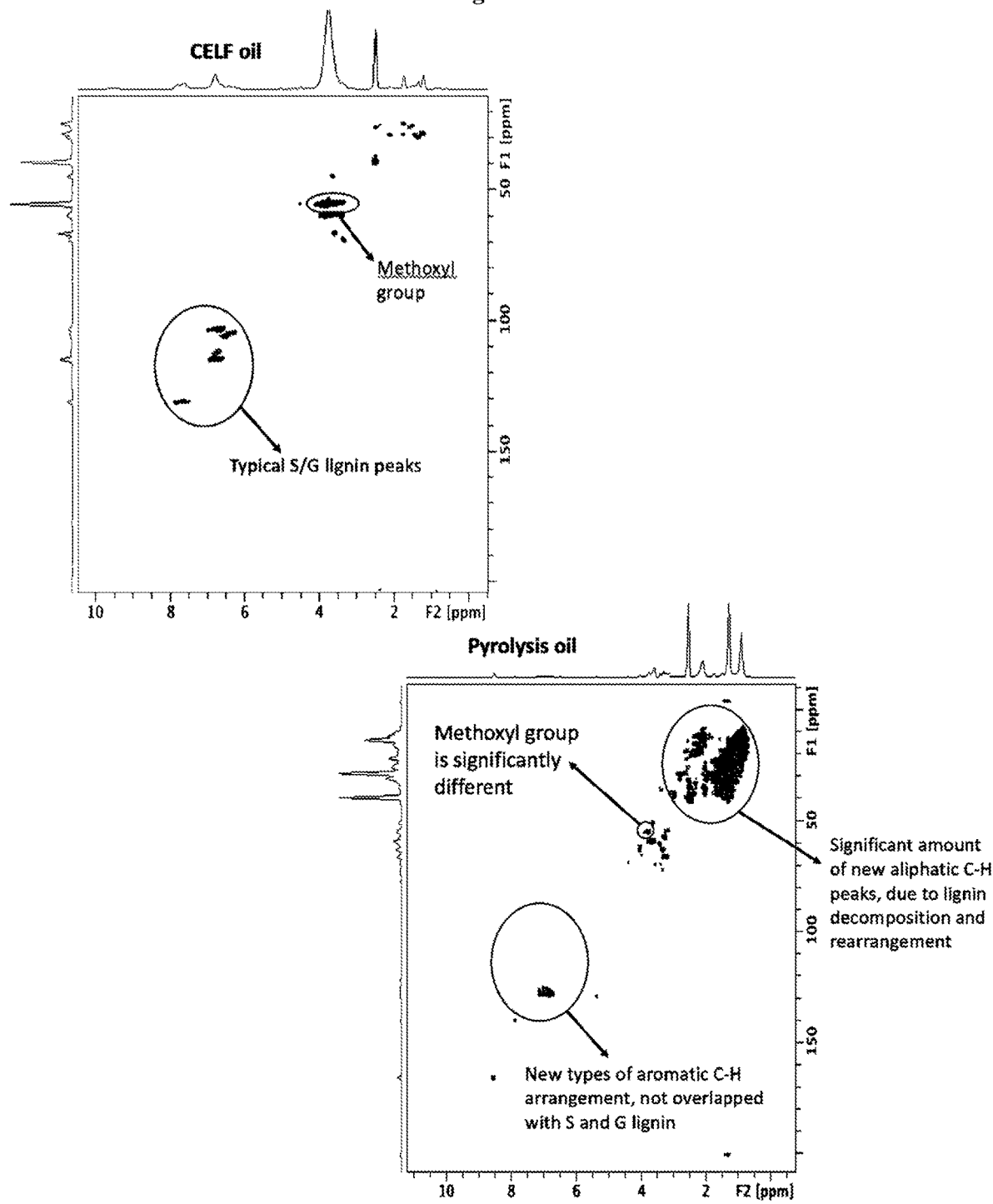
FIG. 6 is a HSQC NMR comparison of the two products in Blendable Oil (specifically Blendable Oil derived from CELF wood oil) as compared to Non-Solvolysis Oil.

Turning to FIG. 6, FIG. 6 as shown is a HSQC NMR comparison of the two products in Blendable Oil (specifically Blendable Oil derived from CELF wood oil) compared to Non-Solvolysis Oil (specifically pyrolysis oil) does not have all the typical peaks (S, G, H, etc) of CELF wood oil and the aliphatic region contains more C—H peaks uncharacteristic of CELF wood oil. Besides that, Non-Solvolysis Oil (i.e., pyrolysis oil) will have a significant amount of other types of aromatic C—H peak (not overlap with typical S/G lignin units) due to the decomposition and rearrangement reactions.

The best way to distinguish them in FIG. 2 would be to look at the aliphatic region: first is two types of methoxyl group exist in pyrolysis oil while only one type of methoxyl group exists in CELF lignin (i.e., from Blendable Oil); second is a significant amount of new aliphatic C—H peaks formed in the C(10-50)/H(0-4) ppm aliphatic region.

The primary constituents of Blendable Oil are depolymerized intermediates from native biomass lignin. The primary constituents of Non-Solvolysis Oil pyrolysis oil are acid fragmented, recondensed, and cross-polymerized products from anhydro-sugars and lignin. During the CELF solvolysis reaction, lignin in native biomass is simultaneously solvated, extracted, and depolymerized with less than 20% re-polymerization occurring between lignin-lignin and lignin-carbohydrate fragments. Without being bound by theory, it is believed that higher temperature thermochemical conversion (i.e., Non-Solvolysis Oil) techniques cause significant repolymerization, cross-polymerization, and condensation reactions of both sugar and lignin intermediates that are detrimental to the product oil's compatibility for blending with RFO, bitumen, coal tar pitch, and other SARA-containing (saturates, aromatics, resins, and asphaltenes) fossil products (therefore in comparison the inventive Blendable Oil is virtually void, preferably less than 50% as compared to non-inventive Non-Solvolysis Oil and particularly preferred less than 90% as compared to Non-Solvolysis Oil, of repolymerization, cross-polymerization, and condensation reactions of both sugar and lignin intermediates). The depolymerized molecular weight lignin fragments comprising Blendable Oil resulting from the CELF reaction are uniquely different in their polarity, arylether content, S:G ratio, and end-group character than the poly-aromatics found in Non-Solvolysis Oil pyrolysis oil or HTL biocrude (DOI: 10.1021/acssuschemeng.8b01028 and DOI: 10.1021/acssuschemeng.8b01930).

Uniquely as well, because CELF wood oil is produced first in a homogeneous solution within the co-solvents THF and water in the CELF liquor, the inventive blending of Blendable Oil with RFO and bitumen can be facilitated and performed by distillative blending. A novel method of distillative blending or incorporating solvolysis oils such as Blendable Oil into residual fuel oils and bitumen achieves blend levels of up to 70%, such that the blended mixture does not immediately phase separate or sediment if the blended product is maintained at a constant storage temperature of >80 C. Hereinafter Blended Product is the combined Blendable Oil with fossil-based components (e.g., RFO, bitumen, etc.). Further, this Blended Product is easily reconstituted into a homogeneous mixture by reheating to >100 C with mild mixing when the Blended Product was previously cooled to below 60 C including for the purpose of cold storage. The Blended Product characteristics, distinctly different than prior art techniques that describes blending of other biomass-derived oils with SARA products, achieved through the inventive blending method is only achievable with Blendable Oil. The Blendable Oil is characterized in this context as a high-boiling or non-boiling oil product contained within solvolysis liquor that is produced during mild acid treatment (at a temperature of below 250 C) of biomass using water-miscible co-solvents (solvolysis) having over 95% of the biogenic carbon-containing components from biomass liquefied or solubilized into the liquor. This means that Blendable Oil is classified as such when their production from biomass resulted in no more than 5% carbon loss to insoluble and gasses during the solvolysis reaction. Unique to solvolysis liquors is that they already contain the necessary Blendable Oil and diluent after reaction to support blending with fossil-derived heavy oils, bitumen, and coal tar pitch. Further, Blendable Oils are fully miscible in solvolysis liquor and do not contain chars. Direct blending of Blendable Oil with RFO and/or bitumen is achieved by distillative blending to produce a stable Blended Product dissimilar to potential blends achieved from Non-Solvolysis pyrolysis oil or HTL biocrude that have limited phase and thermal stability.

Material and Methods

For the inventive solvolysis portion, CELF liquor was produced from pinewood (softwood) and poplar wood (hardwood) chips in a 1 gal continuously stirred autoclave reactor made by Parr® Instruments (Moline, Ill.). The reactor contained a single 6-blade pitched impeller setup. The reactor was heated by electric heating coil (recognized as reasonable approach for laboratory scale only and replaced by methods known in the art for non-laboratory scale). As outlined in Table 1, several reactions on poplar wood were first performed illustrating the impact of temperature, acid concentration, and duration on total liquefaction by CELF. CELF5 was then selected as the ideal temperature (180 C) and acid concentration (0.1M) for biomass liquefaction by acid solvolysis to produce CELF wood oil. For producing CELF5 oil, the following components were added to the reactor prior to heating: 80 g wood chips (4 mm average particle size), 200 g THF, 97 g water, and 3 g sulfuric acid. Heating these contents in the reactor up to 180 C for a residence time of 20-45 minutes was sufficient to produce CELF liquor containing CELF wood oil. Less than 2% solids were found in subsequent vacuum filtration of the CELF liquor through paper filter to determine that complete solvolysis had taken place in all reaction conditions. During the initial heat up and up until the first minute of reaching 180 C, the impeller was not operated due to the high viscosity of the components inside the reactor. Unique to CELF wood oil, mixing is not necessary (i.e. solvolysis process is void of mechanical mixing) to liquefy the biomass as molecular-level interactions between the co-solvents and the biomass substrates were found to be dominant factors in promoting biomass solvation (DOI: 10.1021/jacs.6b03285 and DOI: 10.1039/C5GC01952D). The liquefaction of biomass occurred approximately 30 seconds after 180 C was reached and allowed the gradual increase of the impeller stir rate from 1 rpm to 150 rpm over the course of the next 20 minutes. The CELF liquor reaction was then terminated after 20, 30, or 45 minutes while maintaining the temperature above 170 C by neutralization with Calcium Carbonate or Calcium hydroxide or Calcium Oxide at stoichiometric or slightly above stoichiometric ratios. Without being bound to theory, the reason for extending the reaction duration out to 20-45 minutes is to allow the acid dehydration reactions to sufficiently dehydrate all the biomass sugars into furfurals, levulinic acid, or formic acid that can be recovered more efficiently during later distillative blending. The neutralization in-situ was accomplished by manual operation of a ball valve from a custom-designed tube gas-driven slurry injection device attached to the reactor lid. Alternatively, unneutralized CELF liquor was also produced, however, the CELF wood oil that is subsequently isolated or blended would contain undesirable sulfur or chlorine compounds, but its bulk properties would largely be unaffected. The contents of the reactor were rapidly cooled by circulating chilled water through a coil heat exchanger installed to the reactor. It is understood that acids can be isolated and recovered using methods as known in the art prior to neutralization.

For isolation of only CELF wood oil from CELF liquor without blending, CELF liquor was transferred to a rotary evaporator set to 60 Torr and heated to 60 C. After 4 hours, the volatiles have been mostly recovered leaving behind a residual high boiling CELF wood oil that is primarily composed of biomass lignin. The distilled volatiles have been analyzed by HPLC (Agilent 1200 with FID detector) using an Aminex® HPX-87H column and identified as THF, water, furfural, 5-hydroxymethylfurfural, levulinic acid, formic acid, acetic acid, butanediol, and trace other furans. These volatiles are otherwise known as reactive intermediates and represent all remaining carbon species that are not contained within the CELF wood oil. The mass balance of the volatile and non-volatile fractions of CELF liquor by isolation of CELF wood oil and the reactive intermediates suggest that both acid dehydration and acid hydrolysis are occurring during the CELF reaction, but condensation reactions are limited to below 20% relative to total amount other inter-unit linkages. The limited condensation reactions allow the CELF liquor products to be uniquely more depolymerized and more easily separated from each other.

For the characterization portion of this inventive blending process, CELF liquor generated from poplar wood chips was transferred to a rotary evaporator set to 60 Torr vacuum pressure and heated to 60 C. After 4 hours, the co-solvents THF and water were distilled from the liquor leaving behind only CELF wood oil. This CELF wood oil was then further removed of residual moisture by atmospheric heating in an oven at 60 C for 12 hours. The dehydrated CELF wood oil was then aliquoted and analyzed by GPC and 2D NMR. For GPC, dried CELF wood oil was acetylated in 2.00 mL acetic anhydride/pyridine (1:1, v/v) mixture in a dark room at 21 C. 2 mL ethanol was added after 24 hrs and then the solvents were then transferred to a rotary evaporator set to 60 Torr vacuum pressure and heated to 40° C. The acetylated CELF wood oil was dissolved and then incubated in THF for 24 h. The molecular weight analysis was performed on an Agilent GPC SECurity 1200 system with Waters (Milford, Mass.) Styragel columns at an eluent flow rate of 1.0 mL/min at 30° C. Standard calibration was performed by using polystyrene standards. Quantitative 31P NMR and heteronuclear single quantum coherence (HSQC) NMR spectra were acquired on a Bruker Avance III HD 500-MHz spectrometer at a 90° pulse width, 1.2 s acquisition time, 25 s pulse delay. 20~30 mg samples of CELF wood oil was dissolved in 700 mL pyridine/CDCl3 (1.6:1, v/v) containing chromium(III) acetylacetonate (1 mg/mL). The lignin sample was subjected to NMR analysis promptly after phosphitylating with 2-chloro-4,4,5,5 tetramethyl-1,3,2-dixoaphospholane (TMDP). The obtained 31P NMR spectra were calibrated by using the TMDP-water phosphitylation. The sample was dissolved in 0.50 mL DMSO-d6 in a 5 mm-NMR tube. HSQC experiments were carried out using a N2 cryoprobe (BBO 1H & 19F-5 mm) and a Bruker pulse sequence (hsqcetgpspsi2.2) with the following acquisition parameters: spectra width 12 ppm in F2 (1H) dimension with 1024 data points (acquisition time 85.2 ms), 166 ppm in F1 (13C) dimension with 256 increments (acquisition time 6.1 ms), a 1.0 s delay, a JC-H of 145 Hz, and 128 scans. The HSQC NMR spectra were processed and analyzed by using TopSpin software (version 3.5pl7, Bruker).

For the inventive distillative blending portion, high sulfur residual fuel oil (HSRFO) or marine bunker fuel oil (ISO380 supplied by Shell Oil Company), athabasca bitumen (AB) (purchased online), and coal tar pitch (CTP) (purchased online) were used as the fossil-based blend recipients individually or in combination also referred to as "Fossil-based Blend Recipient". The reactor used was pre-fitted with a vacuum port, a suction port, and a gas outlet port for mass transfer service. The vacuum port was used to pull a vacuum inside the reactor, the section port was used to pull in blend recipients, and the gas outlet port was attached by a Teflon tube to a 1 gal glass round-bottom vacuum trap flask (Chemglass, NJ) that was submerged inside an open-top dewar filled with liquid nitrogen. The gas outlet port and all components attached were placed under continuous vacuum by a vacuum pump. To introduce HSRFO to the CELF liquor in the reactor, it was first placed into a glass bottle on top of a plate heater and heated evenly to 80 C in order to fluidize the heavy residual fuel oil. A mild vacuum was then applied to the 1 gal Parr reactor containing the CELF liquor to achieve suction in order to pull in the heated HSRFO from glass bottle into the reactor vessel. Assuming the volume of the contents inside the reactor prior to blending is approximately 380 mL, HSRFO was sucked into the 1 gal reactor containing CELF liquor and maintained by the sand bath above 100 C. Volumetrically, blend samples containing 10% HSRFO up to 80% HSRFO were made. In order to achieve the Blended Product, HSRFO was first sucked into the heated 1 gal Parr reactor containing CELF liquor. The reactor impeller rotation rate was maintained between 150 rpm and 350 rpm and was increased as more HSRFO was added to the vessel. Upon addition of the HSRFO at volumetric blends of 10%, 30%, 50%, 60%, and 80% with the CELF liquor, the HSRFO suction port was closed and the contents of the reactor were allowed to mix for 5 minutes and reactor temperature was raised to 150 C. The gas outlet port on the reactor lid was then opened to allow gasses to leave the reactor. Over the course of the next 2 hours, all distillates in the CELF liquor including water and THF (i.e., co-solvent of solvolysis reaction) were removed through the gas outlet port by vacuum distillation and condensation into the glass round-bottom flask. Over the course of the vacuum distillation, the impeller was maintained above 200 rpm until the reactor primarily contained CELF wood oil and HSRFO. The simultaneous process of distillation of the CELF liquor continuously mixed with Fossil-based Blend Recipient to produce a Blended Product is the primary objective of this invention. Once no more condensed products are significantly formed in the glass vacuum trap, the blending is terminated, and the stirring is stopped. The gas outlet valve is closed, and the blended contents are poured out of the reactor into a glass media bottle for storage. Using this detailed distillative blending method, simultaneous distillation and blending of the CELF liquor with HSRFO was achieved to create a stable blended oil containing at least 10 wt % and up to 70 wt % biogenic or biomass-derived carbon. Using the aforementioned method, similar blends of CELF oil with AB and CTP were created. All blended products between CELF wood oil and petroleum heavy residual fuel oil, or bitumen, or coal tar pitch will be mentioned as blended CELF wood oils or Blended Product. The Blended Product was then analyzed for trace minerals, CHNS elemental, viscosity, and pour point.

Results and Discussion

It is understood that THF is the particularly preferred solvent within the acid solvolysis process, however GVL, acetone or other water-miscible solvents polar aprotic co-solvents can be substituted for THF. However, GVL's high boiling point makes it very difficult to recover from the liquor. Using the aforementioned methods, the co-solvents THF, water, and other monomeric water-soluble reactive intermediates produced during the CELF reaction are fully dissolved into the CELF liquor. As THF, water, and the water-soluble reactive intermediates can be boiled out of CELF liquor to isolate CELF wood oil, the inventive step of simultaneous distillation and blending of the CELF liquor with a Fossil-based Blend Recipient (fossil-derived residual oil product such as heavy/residual fuel oil, bitumen, or coal tar pitch) to produce a stable Blended Product incorporating the Blendable Oil is achieved.

To understand the dependence of CELF reaction conditions on the liquefaction biomass, several reaction temperatures, acid loadings, and reaction times were executed and identified in Table 1. As shown in Table 1, it was determined that temperature and acid loading had the greatest impact towards liquefaction of biomass. Poplar wood chips were completely liquefied during the CELF reaction for the CELF5 sample that was ran at 180 C, 0.1M of either sulfuric acid or ferric chloride, and 30 mins in a lab scale reactor. The remaining non-soluble mass was primarily composed of insoluble mineral ash as virtually all of the carbon-containing components in biomass were liquefied. Dried CELF wood oil samples from Table 1 were then isolated by vacuum distillation of the THF, water, and reactive intermediates from the CELF liquor using a lab-scale 5 L rotary evaporator. In commercial practice, one would use a distillation unit or vacuum distillation unit. Sample identification of the Blendable Oil products made for these studies are listed in Table 1, along with the total liquefaction by mass of the starting poplar wood chips. The samples of Blendable Oil correspond to the reaction conditions listed in Table 1 and were analyzed by 2D NMR and gel permeation chromatography (GPC), in accordance to the materials and methods section, and the molecular weight, hydroxyl content, and % relative interlinkages are shown in FIG. 1, Table 2, and Table 3, respectively. As shown in Table 2, the molecular weight, hydroxyl composition, and interlinkages are uniquely different from other oil products, such as the well-studied compositions of oils derived from higher temperature (>250 C) biomass liquefaction techniques such as pyrolysis or hydrothermal liquefaction.

For instance, CELF Blendable Oil's β-O-4' aryl-ether interlinkages are nearly (at least 50%, preferably at least 80%, and particularly preferred at least 90%) completely broken with substantial reductions in both β-β interlinkages and β-5 interlinkages. As shown in Table 2, the CELF wood oil isolated from mild CELF treatment (CELF1 and CELF2) demonstrated similar interunit linkage content as lignin from native poplar, showing virtually no condensation and also very little fragmentation or depolymerization (at most 20%, preferably at most 10%, and particularly preferred at most 5%). The oil collected from more severe CELF treatments (CELF3-5) resulted in significantly more fragmentation that is further supported by GPC data (FIG. 1) showing significant depolymerization of the CELF Blendable Oil to low molecular weight components. It is important to note that CELF Blendable Oil is completely hydrophobic and will begin to precipitate from the CELF liquor as THF is first recovered during distillation. Because the water-soluble reactive intermediates found in CELF liquor are pure components, they are also separated out during the distillation to isolate CELF Blendable Oil. This means the inventive process enables the concurrent separation and recovery of lower boiling reactive intermediates and independent of the agglomeration of the residual CELF Blendable Oil. If, during the distillation of CELF liquor, the CELF Blendable Oil agglomeration process is intercepted with other Fossil-based Blend Recipient (e.g., similarly resinous residual products such as residual fuel oil, bitumen, or coal tar pitch), then they can be seamlessly blended together into a Blended Product that is part biogenic and part fossil-derived.

Also, CELF4-5 showed nearly complete cleavage of interunit linkages that outcompeted condensation reactions so that the weight-average molecular weight remained below 4000 g/mol. Non-inventive pyrolysis oils and HTL biocrudes made directly from biomass are typically characterized as having of condensed structures resulting in much greater than 20% new aliphatic character due to significant degree of cross-condensation reactions between anhydrosugars, levoglucosan, furans, and lignin that result in an oil product containing 15-50% water content. The highly condensed nature of pyrolysis oil and bio-crude is further characterized by insoluble char and heavy tar formation. The components that make up pyrolysis oil and bio-crude comprise of molecules are too cross-linked and polar to achieve a high degree of solvation with petroleum residuals, bitumen, and coal tar pitch and therefore do no yield uniform blends of bio-derived oils with fossil-based oils.

TABLE 1

CELF reaction conditions and % liquefaction of hardwood poplar.

| Lignin sample | Acid (M) | Temperature (° C.) | Duration (min) | Liquefaction (%) |
|---|---|---|---|---|
| CELF1 | 0.025 | 150 | 15 | 35 |
| CELF2 | 0.05 | 150 | 15 | 41 |
| CELF3 | 0.05 | 160 | 15 | 48 |
| CELF4 | 0.05 | 180 | 15 | 83 |
| CELF5 | .1 | 180 | 20-30 | 98+ |

TABLE 2

CELF oil's hydroxyl contents determined by quantitative $^{31}$P NMR analysis.

| hydroxyl, mmol/g lignin | CELF1 | CELF2 | CELF3 | CELF4 | CELF5 |
|---|---|---|---|---|---|
| aliphatic | 4.55 ± 0.04 | 3.94 ± 0.01 | 2.45 ± 0.05 | 1.11 ± 0.02 | 1.07 ± 0.02 |
| phenolic | 1.56 ± 0.05 | 1.71 ± 0.05 | 2.18 ± 0.03 | 3.05 ± 0.01 | 2.81 ± 0.05 |
| carboxylic | 0.08 ± 0.01 | 0.07 ± 0.01 | 0.10 ± 0.01 | 0.15 ± 0.00 | 0.17 ± 0.02 |
| total | 6.19 ± 0.08 | 5.72 ± 0.05 | 4.72 ± 0.08 | 4.31 ± 0.03 | 4.04 ± 0.09 |
| C$_5$-substituted | 0.76 ± 0.03 | 0.9 ± 0.02 | 1.30 ± 0.01 | 1.71 ± 0.01 | 1.71 ± 0.02 |
| guaiacyl | 0.50 ± 0.02 | 0.54 ± 0.03 | 0.67 ± 0.02 | 1.02 ± 0.00 | 0.97 ± 0.00 |
| p-hydroxyphenyl | 0.30 ± 0.01 | 0.28 ± 0.01 | 0.21 ± 0.00 | 0.22 ± 0.00 | 0.13 ± 0.01 |

TABLE 3

Semiquantitative analysis of CELF wood oil's lignin subunits compared to native lignin isolated from poplar wood.

| Lignin Subunits (%) | Native lignin | CELF3 | CELF5 |
|---|---|---|---|
| syringyl | 60.9 | 56.8 | 44.3 |
| guaiacyl | 39.1 | 43.2 | 55.7 |
| p-hydroxybenzoate | 14.3 | 13.6 | 17.5 |
| S/G ratio | 1.6 | 1.3 | 0.8 |
| Interlinkages (%) | | | |
| β-O-4 | 61.1 | 9.2 | ND |
| β-β | 4.7 | 1.9 | 0.04 |
| β-5 | 5.4 | 1.8 | ND |

Due to the selective hydrolysis and dehydration reactions that occur to both the carbohydrates (sugars) and lignin fractions in biomass during CELF acid solvolysis, the carbohydrates are primarily transformed at high yields into the reactive intermediates furfurals, levulinic acid, and formic acid that can be recovered by distillation so that they do not further cross-polymerize or condense with the resinous lignin fraction and also distinguishing CELF Blendable Oil as containing a water content of less than 5%.

The CELF reaction temperatures are also far reduced (at least 100 C lower, preferably lower than 250 C, and particularly preferred less than 200 C) compared to pyrolysis and HTL such that that acid fragmentation and acid hydrolysis are the dominant reactions, allowing separation between the water-soluble and water-insoluble components of CELF liquor by their boiling points; CELF Blendable Oil is the high boiling water-insoluble portion of CELF liquor and the reactive intermediates along with the co-solvents are the low boiling water-soluble portion of CELF liquor. As THF is removed from the CELF liquor, the CELF Blendable Oil components begin to agglomerate. During this agglomeration of CELF Blendable Oil within CELF liquor, it can be amenable to blending with other non-polar resinous oils, such as petroleum-derived residual oils, bitumen, and coal tar pitch. In fact, all three aforementioned fossil-based products are fully miscible in CELF liquor due to the presence of THF. This means that if the fossil-residual products were dissolved first into CELF liquor, that simultaneously distilling and blending the CELF liquor afterwards would be an efficient way to make a stable blended oil (the inventive Blended Product) containing both biomass and fossil-based products. The product of this simultaneous distillation and blending method is unique from other biomass/fossil oil blends because the Blended Product can be filtered through a 2-micron screen, can be indefinitely reconstituted, and can maintain phase-stability and thermal-stability when stored hot.

Blended Product containing 50-70% biogenic carbon was determined to be phase-stable and thermally-stable at temperatures above 100 C. Meaning, that the Blended Product can optionally be reconstituted into a homogeneous liquid oil by heating the Blended Product to exceed its average melting point (>100 C) such that the heated Blended Product can pass through a 2 micron filter with greater than 98 wt % pass-through efficiency. Blended Product containing of 25-50% biogenic carbon is phase-stable and thermally-stable at temperatures above 80 C. Blended Product up to 25% biogenic carbon is phase-stable and thermally-stable at temperatures above 50 C. As there is very little water in the Blended Product, phase and thermal stability was observed as the ability for the Blended Product to maintain bulk homogeneity without sedimentation upon filtration. Another feature of this Blended Product is that it can be cooled to room temperature for storage, but its high viscosity will not allow appropriate determination of the homogeneity. In fact, the Blended Product is 10-50% more viscous than their unblended Fossil-based Blend Recipients. An inventive feature is that upon heating the cooled Blended Product back up, the Blended Product will again return to its stable morphology. As woody biomass contains very little water-insoluble minerals and sulfur, it was determined that trace elements found in fossil products such as sulfur, vanadium, calcium, and silicon can be proportionally reduced by blending with Blendable Oil. This would have drastic implications to improving both the carbon intensity and quality of residual fossil fuels.

As increasing pressure from environmental policies demand reduced sulfur, reduced toxic emissions, and reduced life cycle GHG emissions in current petroleum-related and petroleum-dependent industries, we believe that Blendable Oils are positioned uniquely to solve these challenges without significant alteration of existing infrastructures. Due to the stability of the Blended Product, it can be used to displace petroleum in existing manufacturing or processing infrastructures that use heavy oil oils, bitumen, and coal tar pitch. For example, heavy marine fuel could be simply blended with Blendable Oil to produce a blended marine fuel with proportionally reduced sulfur content and maintain physical stability for combustion in marine vessels.

In another example, Athabasca bitumen could be directly blended with Blendable Oil to take advantage of the biogenic incorporation leading to carbon intensity reductions during bitumen processing while also improving the quality of the coke product. Finally, coal tar pitch can be blended with Blendable Oil in order to reduce sulfur and unwanted trace minerals to improve the quality of the pitch as a resin binder for the production of aluminum anodes. Blendable Oil also enables industries to gradually adopt to a new feedstock without supplanting existing operations. As more research, analytics, and performance data is acquired from the Blended Products starting from a smaller % blend of Blendable Oil, process and product development can catch up to support increased blending proportions without detrimental impact to reliability and performance.

The Blended Product can further be co-optimized with medium-speed and low-speed reciprocating engines in stationary applications to generate electricity or power. In this configuration, both the heat and power produced from stationary generation capabilities can support modular power systems that can be deployed in remote regions such as rural communities, impoverished communities, or battlefields to decrease the need and costs of transporting petroleum fuel to these regions. The co-optimizing process includes viscosity modification, additives that promote more complete combustion therefore resulting in lower soot production, and additional additives as known in the art.

Although the invention has been described in detail, regarding certain embodiments detailed herein, other anticipated embodiments can achieve the same results. Variations and modifications of the present invention will be obvious to those skilled in the art and the present invention is intended to cover in the appended claims all such modifications and equivalents.

What is claimed is:

1. A process for making a blended product, the process comprising: an acid solvolysis or a co-solvent liquefaction of a lignocellulosic biomass into a homogenous liquid product carried out at a temperature of less than 200 C to generate a solvolysis liquor comprises an at least one component of a lignocellulosic biomass as a liquified biomass and an at least one of a co-solvent used in the liquefaction, and a water; wherein a heating process of a fossil-based blend recipient whereby the fossil-based blend recipient is pre-heated to a temperature of greater than 80 C; wherein the solvolysis liquor and the pre-heated fossil-based blend recipient are subsequently combined to produce a blended solvolysis liquor; wherein the blended solvolysis liquor and the pre-heated fossil-based blend recipient subsequently undergoes a simultaneous distillation and blending process wherein the blending process removes the at least one of the co-solvents and any low-boiling components resulting in the blended product; wherein the simultaneous distillation and blending process emulsifies a high-boiling or non-boiling residual fraction from the blended product, wherein the simultaneous distillation and blending process results in the solvolysis liquor having a co-solvent soluble fraction that forms a stable emulsion with the fossil-based blend recipient; wherein the stable emulsion does not rapidly settle into two distinct phases when maintained at a temperature of 100 C or greater, and wherein the blended product comprises a 10 wt % to a 80 wt % of a biogenic or biomass-derived carbon.

2. The process for making the blended product according to claim 1 whereby the acid solvolysis utilizes the co-solvent and the water, and whereby the co-solvent is tetrahydrofuran.

3. The process for making the blended product according to claim 1 whereby the fossil-based blend recipient is pre-heated to a temperature of greater than 100 C.

4. The process for making the blended product according to claim 1 whereby the acid solvolysis is at a solvolysis temperature greater than 170 C.

5. The process for making the blended according to claim 1 whereby the solvolysis liquor has been removed of the water and whereby the process to remove the water is void of sedimentation and precipitation of insoluble products.

6. The process for making the blended product according to claim 1 whereby the co-solvent-soluble fraction of the pyrolysis liquor is void of a condensed tar or char.

7. The process for making the blended product according to claim 1 whereby the blended product contains up to 70 wt % biogenic or biomass-derived carbon.

8. The process for making the blended product according to claim 1 whereby the blended product does not immediately phase separate or sediment when the the blended product is maintained at a constant storage temperature of greater than 80 C.

9. The process for making the blended product according to claim 1 whereby the blended product is reconstituted into a homogeneous mixture by reheating to greater than 100 C with mild mixing after the blended product was previously cooled to below 60 C including cooling for the purpose of cold storage.

10. The process for making the blended product according to claim 1 whereby the acid solvolysis co-solvent is also a diluent for the fossil-based blend recipient and whereby the fossil-based blend recipient is fully miscible in the solvolysis liquor.

11. The process for making the blended product according to claim 1 wherein the acid solvolysis is at a solvolysis temperature at or below 180 C.

12. The process for making the blended product according to claim 1 whereby the acid solvolysis process is void of mechanical mixing in liquefying the lignocellulosic biomass feedstock through molecular-level interactions between the co-solvent and the lignocellulosic biomass feedstock.

13. The process for making the blended product according to claim 1 whereby the acid solvolysis process has an acid hydration reaction and whereby the acid hydration reaction is terminated after dehydrating the lignocellulosic biomass feedstock into at least one sugar and whereby the at least one sugar is dehydrated into at least one of a furfural, levulinic acid, or formic acid for recovery during the simultaneous distillation and blending process.

14. The process for making the blended product according to claim 1 wherein the liquified biomass is virtually void of a tar or a char or any components derived from pyrolysis or hydrothermal liquefaction within the solvolysis liquor; whereby the blended product composition comprises a fossil-based blend recipient and a high-boiling or non-boiling residual fraction derived from a lignocellulosic biomass feedstock; wherein the high-boiling or non-boiling residual fraction is characterized by a 2D Heteronuclear Single-Quantum Correlation-Nuclear Magnetic Resonance to be virtually void of a C1 type of a methoxyl group or ether bond in an ortho position of the methoxyl group and a native biomass lignin; and wherein the blended product has at least 10 wt % of a biogenic or biomass-derived carbon.

15. The process for making the blended product according to claim 14 wherein the high-boiling or non-boiling residual fraction is characterized by a 2D Heteronuclear Single-Quantum Correlation-Nuclear Magnetic Resonance with the presence of lignin inter-linkages including β-aryl ether, phenylcoumaran, and resinol subunits in the aliphatic region.

16. The process for making the blended product according to claim 1 whereby the acid solvolysis utilizes the co-solvent and the water, and whereby the co-solvent includes gamma-valerolactone.

17. The process for making the blended product according to claim 1 whereby the acid solvolysis utilizes the co-solvent and the water, and whereby the co-solvent includes acetone or other water-miscible polar aprotic co-solvents.

18. The process for making the blended product according to claim 14 wherein the blended product has a water content of less than 5%.

19. The process for making the blended product according to claim 14 whereby the blended product is filtered through a 2-micron screen, can be indefinitely reconstituted, and maintains phase-stability and thermal-stability when stored at a temperature greater than 100 C.

20. The process for making the blended product according to claim 14 wherein the fossil-based blend recipient is either a heavy marine fuel or a residual fuel oil having a proportionally reduced sulfur content, and whereby a physical stability of the blended product is maintained for a combustion process in a marine vessel; a bitumen having a proportionally reduced sulfur content; or a coal tar pitch to improve a coal tar pitch quality that is subsequently used as a resin binder for the production of an aluminum anode.

* * * * *